United States Patent

Snook

[11] Patent Number: 5,886,767
[45] Date of Patent: *Mar. 23, 1999

[54] KERATOMETRY SYSTEM AND METHOD FOR MEASURING PHYSICAL PARAMETERS OF THE CORNEA

[76] Inventor: Richard K. Snook, 8050 N. Tackroom Ln., Tucson, Ariz. 85741

[*] Notice: The term of this patent shall not extend beyond the expiration date of Pat. No. 5,735,283.

[21] Appl. No.: 753,384

[22] Filed: Nov. 25, 1996

Related U.S. Application Data

[63] Continuation-in-part of Ser. No. 727,920, Oct. 9, 1996, Pat. No. 5,735,283.

[51] Int. Cl.$^6$ .................................................. A61B 3/10
[52] U.S. Cl. .......................... 351/212; 351/247; 351/211; 600/558
[58] Field of Search .................................. 351/205, 211, 351/212, 221, 247; 600/558

[56] References Cited

U.S. PATENT DOCUMENTS 3,169,459  2/1965  Friedberg et al. .................. 351/212
4,761,071  8/1988  Baron ................................. 351/212
5,735,283  4/1998  Snook ................................. 351/212

*Primary Examiner*—Huy Mai
*Attorney, Agent, or Firm*—Robert J. Schaap

[57] ABSTRACT

This invention relates to certain improvements in the art of keratometry and, more particularly, to the use of television techniques to determine the shape of the corneal surface of an eye in essentially real-time. Paired television images of diffuse reflections from the cornea are produced by projecting an infra-red illuminated pattern onto the cornea. These diffuse reflections are compared by triangulation to define the corneal contour. The resultant data are processed by a conventional microcomputer to derive surface contour for display, the shape data so generated in a form for instant use. Compensation for image brightness at each location is provided by altering projected image brightness to compensate for inherent non-linearity of diffuse image brightness versus position in the image plane. The liberalization reduces the complexity of the digital signal processing required for producing a contour map of the cornea. The present invention specifically relates to devices that are used in clinical practice.

22 Claims, 4 Drawing Sheets

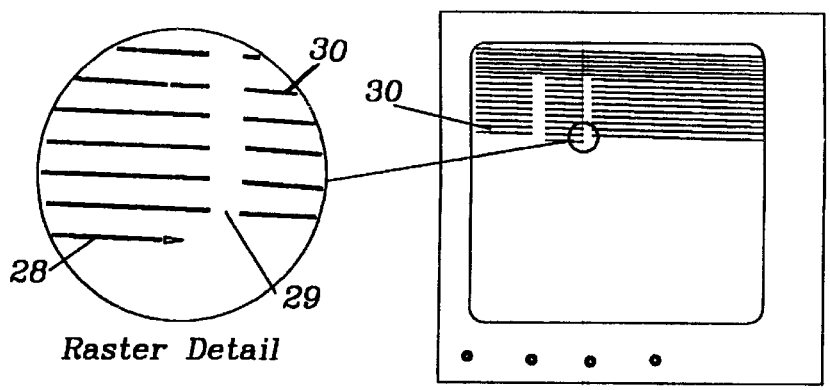
*Fig. 5a*      *Fig. 5*
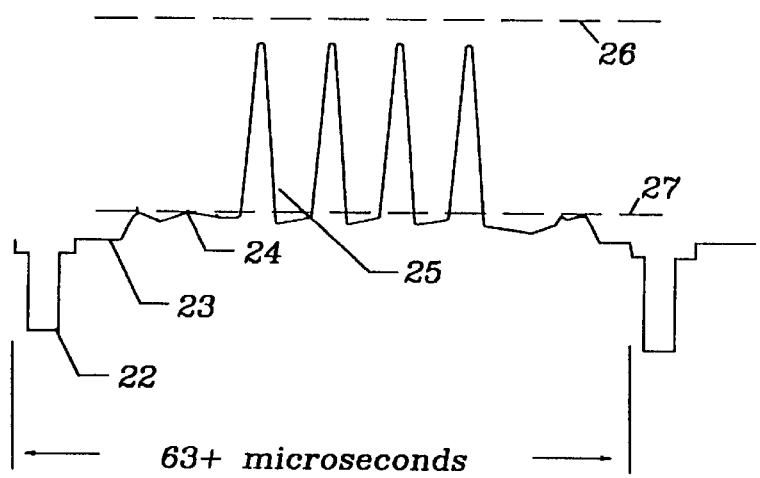
*Fig. 6*
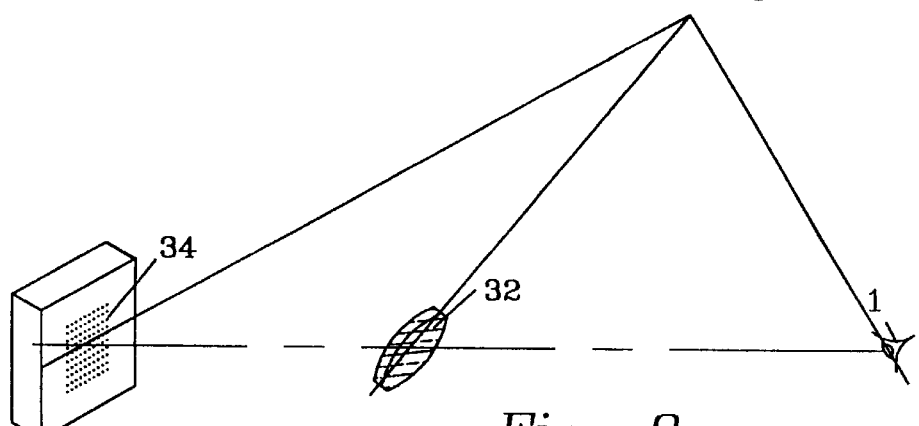
*Fig. 8*

KERATOMETRY SYSTEM AND METHOD FOR MEASURING PHYSICAL PARAMETERS OF THE CORNEA

RELATED APPLICATION

This application is a continuation-in-part of my co-pending U.S. patent application Ser. No. 08/727,920, filed Oct. 9, 1996, for "A Surgical Keratometer System" (now U.S. Pat. No. 5,735,283, dated Apr. 7, 1998).

BACKGROUND OF THE INVENTION

1. Field of the Invention

The present invention relates generally to photo-keratometry, and more particularly, to improvements in the art of photo-keratometry wherein a diffuse reflection of a projected, illuminated surface or other target is formed on the cornea. This diffuse reflection is analyzed to determine the surface contour of the eye. The present invention specifically relates to devices that are used for clinical keratometry

2. Description of Related Art

The instruct that is in most common use for central-optical-zone shape measurement, in ophthalmic clinical practice, is the EyeSys topographer. Several companies offer similar devices, from outright copies to apparatus redesigned using a similar principle of operation. These devices require the user to operate one or more controls. These controls are employed to bring Mire images that are reflected from the tear film on the surface of the eye, simultaneously into focus and alignment.

Most prior art devices require that the tear film on the eye surface be intact since reflection from this film is central to the measurement technique. The tear film is typically not constant in thickness and, in some cases, may not be present at all. This variable thickness or outright absence of the tear film prevents meaningful measurements of the corneal shape. In addition, if the corneal surface is not smooth as in the case of corneal transplants, the reflections are ambiguous and do not permit meaningful determination of the surface shape.

Representative of video keratometers is the EyeSys System 2000. A placido (bulls-eye target) is illuminated by an internal lamp system, and a video image of the reflex is examined by conventional video analysis means. A second generation of these instruments provides for analysis of both corneal surface contour and shape/location mapping of more posterior elements such as corneal thickness, anterior chamber depth and lens geometry. Representative of these is the Orbtek Orbscan. In this instrument, a sequence of optical slit images are formed by conventional projection means and the resulting Tyndall images are used for determination of the mapping information. Requirement for a sequence of images requires that the subject be able to fixate perfectly for a long period of time without either head or eye movement and the large amount of data collected requires extensive calculations which require expensive computers for data analysis.

Prior art systems, however, are costly, complex, and slow, and modifications, if required, are difficult to implement. Thus, it follows that another system for characterizing the eye must be employed in order to produce a functional instrument within the speed and cost constraints required for commercial viability. Additionally, a practical system must be suitable for operation by unsophisticated users. These above-listed factors, as well as other criteria, require a departure from the traditional techniques for keratometry and image analysis.

In recent times, keratometers have been more commonly used in both clinical and surgical ophthalmology and optometry. In spite of the number of systems in use today, universal satisfaction with the results of these systems have not been obtained.

None of the currently available video keratometers, however, are designed to overcome most of these above-mentioned problems. Additionally, the prior art systems exhibit a wide range of error and are inconvenient to operate.

Thus, there remains a need for an apparatus and method for measuring the optical components of the eye that avoids most, if not all, the foregoing problems.

SUMMARY OF THE INVENTION

In accordance with the present invention, an instrument is provided for measuring surface topography and thickness of a cornea. The comprises the following:

(a) an optical projector that projects a pattern onto the cornea, the pattern comprising a plurality of isolated points;

(b) a first camera and a second camera each comprising a camera lens and a detector array, the first camera, the second camera, and the projector directed toward a single point, the first camera and the second camera producing images of the plurality of isolated points projected on the cornea, with the location of each of the isolated points on the cornea being dependent upon the surface topography;

(c) a viewfinder for use in the positioning and alignment of the instrument;

(d) a computer processor that employs triangulation calculations to determine the surface topography from the location of the isolated points on the cornea; and (e) a display for displaying the surface topography.

The method of the present invention, which is intended for measuring both surface topography and local thickness of a cornea, comprises the following steps:

(a) projecting a pattern onto the cornea using a projector, the pattern comprising a plurality of discrete points, the location of each of the discrete points on the cornea being dependent upon the surface topography;

(b) directing a first camera, a second camera, and the projector toward a single point in space;

(c) placing the cornea at a position between the single point in space and the first camera, the second camera, and the projector;

(d) obtaining images of the discrete points projected on the cornea with the first camera and the second camera;

(e) employing triangulation calculations to determine the surface topography and tissue thickness from the location of the discrete points on the cornea; and (f) displaying the surface topography.

The object of this invention is to provide an improvement in the art of photo-keratometry as employed in clinical practice where the measurement of diffusely reflected image points projected on the cornea is analyzed, and the corneal curvature with local thickness information is derived. A second object of this invention is to construct a system that imposes only a low cost on the user and thereby makes the system competitive in the marketplace. An additional object is to include automatic derivation and display of corneal radii with the corresponding axis of measurement. Another object of the invention is to develop a "user friendly" system that is operable without any special training or skill and that produces quick and accurate readings of corneal data. A further object of this invention is to offer an improvement in the art of image analysis, as applied to keratometry and similar measurements, and to reduce the complexity of the computations (as well as apparatus) thereby permitting almost "real-time" analysis.

BRIEF DESCRIPTION OF THE DRAWINGS

FIG. 5 is an illustration of image formation by a television "raster" on a monitor;

FIG. 5a is a magnified view of a small portion of the raster;

FIG. 6 on coordinates of voltage and time (in seconds), is a plot of the television signal waveform;

FIG. 8 is a perspective view depicting the Scheimpflug construction of the present invention.

DESCRIPTION OF THE PREFERRED EMBODIMENTS

Figure 1:
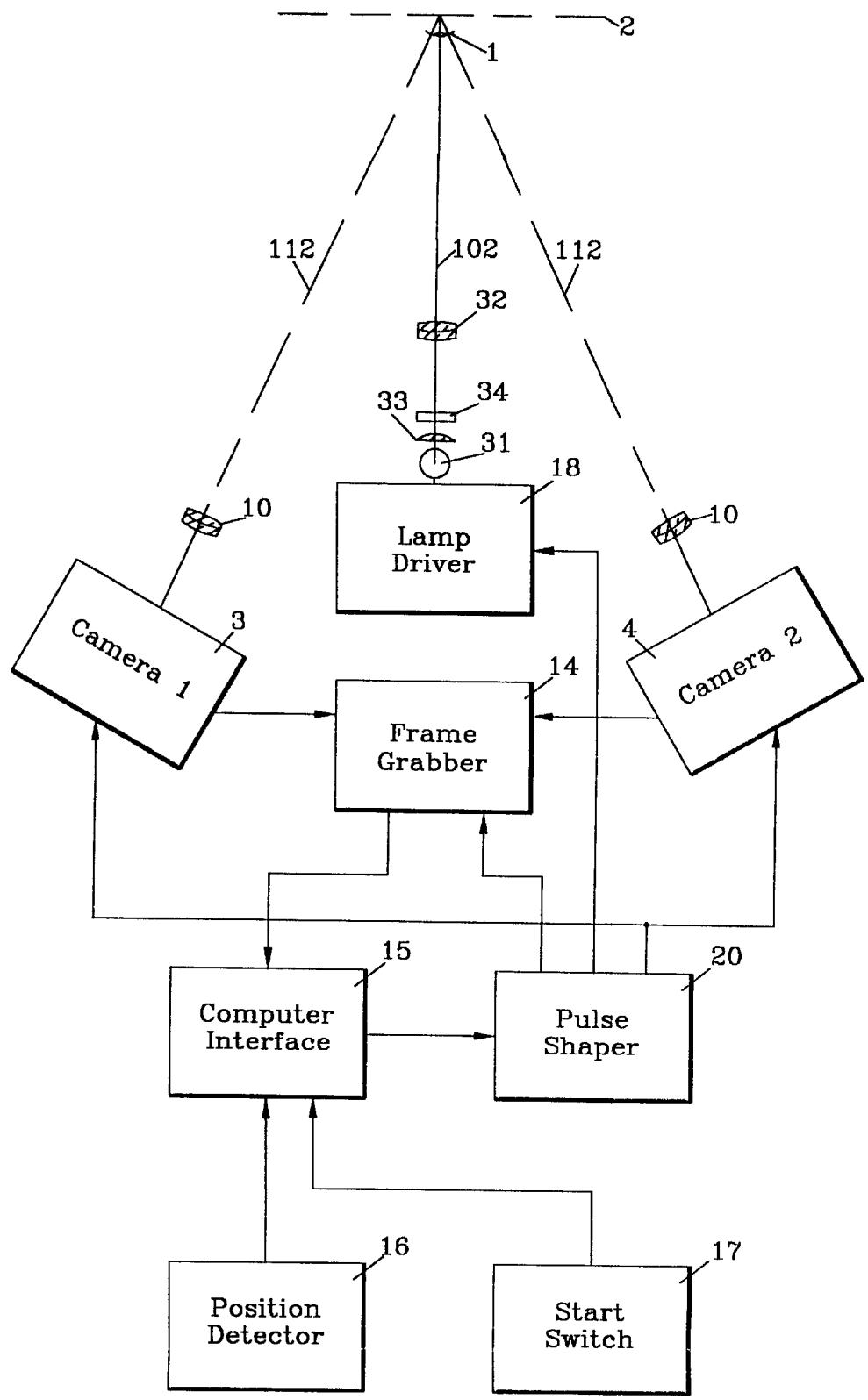
FIG. 1 is a diagram depicting the system of the present invention.

Reference is now made in detail to a specific embodiment of the present invention, which illustrates the best mode presently contemplated by the inventor for practicing the invention. Alternative embodiments are also briefly described as applicable.

After a review of the historical and current is instrument literature, several experiments were made that led to the present invention, which is directed to a method and apparatus for characterizing the shape and local thickness of a human cornea for clinical diagnostic purposes.

In the present invention, a plurality of illuminated target points are projected onto the eye while paired television cameras, which are connected to a computer, are employed to anal the corneal shape of the eye using stereo photogrammetric techniques. In particular, the formation of a series of points in the focal plane of a projector of conventional design produces diffuse reflections within the bulk of the corneal tissue. These points are viewed by paired television cameras mounted at known angles to the axis of projection. The television cameras produce stereo pairs of the images that are in temporal and spatial registration The paired television images are used to define the topography of the corneal surface by a process of triangulation within the associated computer for display to the user while a surgical process is performed.

To locate a point on the outer corneal surface by the triangulation method, the location in three space of several points is established, that is the front principal point for each of the three lenses, The distance from each to the point of intersection of the principal rays (optical axes of each). Any ray in the system may be defined from these by calibration of the cameras image in conjugate form. A ray to a point on the corneal surface has a mathematical description of y+U+Vr, where the (x,y,z) vector U defines the ray origin at the principal point in the camera lens, the vector V establishes direction from the same point and the scalar r is the distance from the origin to the ray point. Direct triangulation then is by intersecting rays from defined points. The diffuse image of the target points is in the form of ovals which have characteristics definable to sub pixel accuracy from calibration data. Circular object plane referred spots assume the shape of two overlapping nearly circular areas with common tangents on both sides. By establishing the direction in x,y terms from the image, the meridional direction may be derived. Midway between these nearly parallel lines is an axis line. The center of the circular images must lie on this line within a small error band caused by local surface slope change. The local slope change for human corneas capable of producing an acceptable image at the retina is quite small and this term may be ignored for clinical use were the exact surface definition need not be closer than one quarter diopter. Because the spot projection was circular, the distance between the centerline established in the previous step can be used from the edge closest to corneal center along the meridian established by the line midway between edges of the reflection. This point is then located by using the calibration source data which defines the outer surface of the illuminated spot which is assumed to be circular around the defined point. The mathematical representation of this circle can be written as f(x)=0 where the vector x represents the (x,y,z) coordinates of a valid point and direct triangulation takes the form of finding a value for r such that f(U+Vr)=0 Since there are two simultaneous solutions for each surface point from the data derived from simultaneous camera images of all surface points the accuracy of the surface point definition can be enhanced or ambiguous point definitions discarded prior to the construction of a corneal map from the data.

The location of the circular area at the other (distal) end of the reflection can then provide local corneal thickness since the index of refraction of the cornea and covering tear film are well established. By derivation of a second surface map from these points, the inner surface of the cornea can be mapped in three space which, in turn, provides the basis for corneal thickness derivation over the entire corneal surface. By detection of the much less bright reflections from the anterior surface of the lens using the same process, the anterior chamber geometry is defined as is the surface shape of the anterior of the crystalline lens. All of the data required for these definitions are obtained in one thirtieth of a second where fill frame data is used or, when single field data are used, the data collection requires one sixtieth of a second. This very short period greatly reduces the errors encountered by prior art systems caused by micro saccadic movement of the eye while the data is being gathered from several sequential frames of video information.

The corneal surface is best described as a prolate ellipsoid with a shape factor of about 0.78 for normal corneas. The mean surface from the map data may be examined in terms of deviation locally from a surface of revolution. The numerical value for best fit is, of course, derived for each cornea measured. This idealized surface is subtracted from the measured surface to define the areas of poor fit and the magnitude of error for these areas. A conic surface of revolution is axisymetric and so have no on axis astigmatism while the actual corneal surface may have considerable astigmatism. The difference mapping technique illustrates the axis and magnitude of any corneal astigmatism which is if great interest to the ophthalmologist or optometrist. FIG. 1 shows a block diagram of the apparatus of the present invention. The apparatus of the present invention comprises an optical bench assembly mounted on a conventional X, Y, Z movement base, an associated headrest system of conventional design and a computer system for receiving and interpreting the images from the optical bench assembly and displaying the interpreted corneal topographic and pachymetric measurements for clinical analysis.

To process the images formed in the cornea, a video signal from the paired television cameras 3,4 is routed to a frame grabber 14, and a computer interface 15. The computer interface 15 provides system timing and control for accepting and storing the sequential paired pictures from the television cameras 3, 4. The data stream from the digitized pictures is routed to an associated computer (not shown) for analysis. The computer via the computer interface 15 also provides video timing information via the pulse shaper 20 to all of the video devices and the lamp 31 to insure the simultaneous capture of the desired paired images of the pictorial sequence.

The calculated result of surface shape in graphical form, is displayed on a conventional video display (not shown).

In most, if not all, cases the exact surface contour of the eye 1 is of less interest to the clinician than the relative contour. For example, in a corneal transplant surgical case, the object is to adjust suture tension and location to arrive at a smooth, regular surface that has a similar contour in two perpendicular axes and is close to the preoperative values (i.e., the induced distortion of the corneal surface is minimal). The errors of measurement are least at (or near) the center of the cornea, and the main image forming surface is encompassed by the same area. This fact permits the system of the present invention to be used in one configuration with a single target matrix projector. In an alternative embodiment, the projection system employs a so-called "zoom lens" in place of the projector lens 32 for determining the area of the corneal surface to be mapped. This allows for changing target image size so that the effective resolution may be enhanced by selecting a small area for analysis. The frame grabber is preferably of the type designed for so called R, G, B video signals. The normal usage of this type frame grabber is to digitize the three primary color portions of a color television signal. In this application the paired television cameras, 3,4 provide the analog video input to two of these input ports. The third signal port may, in an alternative construction (not illustrated), simultaneously digitize the output of a third camera used as a viewfinder. Because these frame grabbers are designed to provide a set of time synchronous conversions to be stored by conventional means in the computer memory, this permits temporal and hence spatial coherence between the television pictures from the television cameras 3.4. The operational sequence is to capture an image pair of the eye and on the next frame capture the same signals except that the target illumination is enabled. The numerical brightness of each picture element will be very similar for most of the paired images differing only where the target images produce diffuse reflections. By numerical subtraction of the defined image pair from each television camera the static image of the eye will be effectively canceled. The remaining numerical information above the noise threshold will contain the Tyndall image which is used for defining the corneal topography and local thickness.

Simultaneous capture of the paired images insures that there is no movement induced error in the spatial definitions derived.

Figure 2:
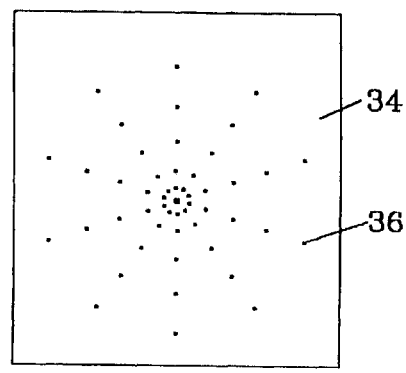
FIG. 2 is a schematic representation of the target matrix.

Refer now to FIG. 2, which illustrates one version of the target matrix 34, an opaque, planar surface is provided with a plurality of transparent points 36 of small area that are arranged in a predetermined pattern. It will be appreciated that the pattern is not limited to the arrangement of transparent points 36 shown in FIG. 2, but may comprise any pattern of discrete points. The image of these points 36 formed by Rayleigh scattering within the bulk of the corneal tissue provides the data points that are used for defining corneal surface geometry in three dimensions.

Figure 3:
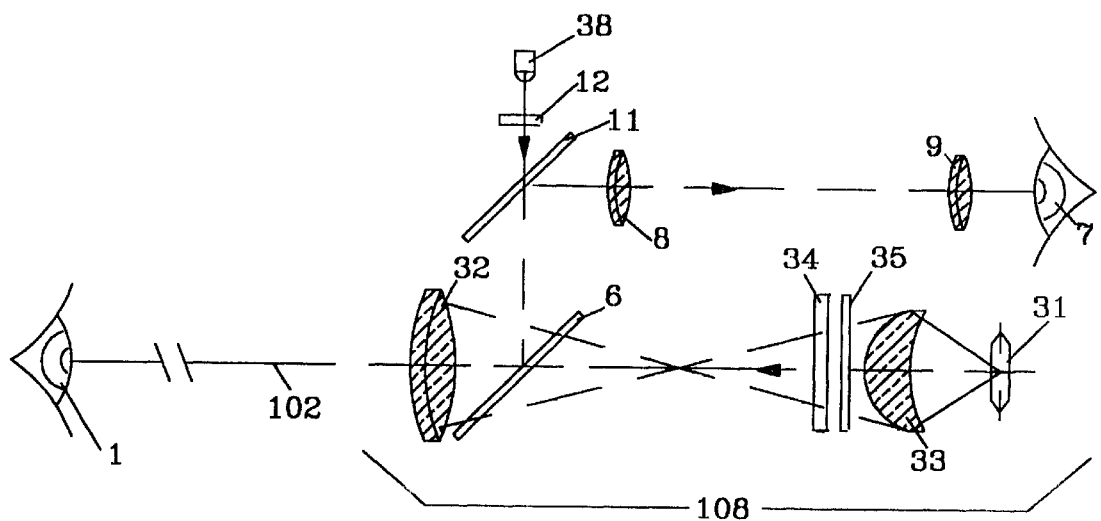
FIG. 3 is a cross-sectional view depicting the projector employed for producing a pattern image on the cornea.

To form an image of the target matrix 34 onto the eye 1, a projector system is employed. FIG. 3 shows a conventional projector system 108, The object to be illuminated, target matrix 34, is an opaque plate with a matrix of small apertures, i.e., transparent points 36. The age of these point sources 36 is formed at the corneal surface. As shown in FIG. 3, the projector system 108 includes a light source 31, a condenser lens 33, and a projector lens 32. It will be appreciated that a small numerical aperture for the projection lens 32 assures adequate depth of focus so that the spots defined by diffuse reflection of the imaged points are sharply defined over the depth of the anterior chamber and corneal thickness. An annular zone type neutral density filter 35 mounted between the matrix or target plate 34, serves to reduce the illumination in an inverse parabolic manner to compensate for image brightness diminution at points remote from center rendering the digitized image more nearly linear for photometric purposes. A small fixation lamp 38, illuminates a photographic slide 12, placed just inside the focus of the projector lens 32. This serves as a target to be viewed by the subject to align the axis of vision with the instrument's optical centerline and to minimize small involuntary eye movements which could degrade the measurement. A pair of beam splitters 6 and 11, permit the mounting of the fixation target and illumination system for viewing by the subject while retaining the projected image at the cornea being examined. An erector lens 8 and an eye lens 9, permit the user's eye 7, to be placed behind the instrument for viewing the eye being photographed. This alignment telescope system may, alternatively, be replaced by a third television camera in an alternative construction (not shown).

As described above, the projector system 108 enables the set of illuminated points 36 in the object plane of the projector to be projected by the projection lens 32 onto the surface of the eye 1. The projection of these points 36 are viewed by the paired television cameras 3 and 4 mounted at known angles to the axis of projection (centerline 102). Accordingly, the television cameras 3,4 produce stereo pairs of the diffuse reflections within the bulk of the corneal tissue. These paired television images are used for defining the corneal surface topography by a process of triangulation.

An essential feature of the apparatus of the present invention is that the optical axes (centerline 102) of the projector 108, and the optical axes 112 of the cameras 3,4 converge at a single point in three space. The optical axes 112 of the cameras 3,4 are defined by the ray that goes through the principal points of the camera lens 10. Similarly, the optical axes 102 of the projector 108 is defined by the ray that goes through the principal points of the projection lens 32.

If the beam from the projector 108 had not been intercepted by the cornea, it would have reached a plane 2, defined by the intersection of these three optical axes (i.e., centerline 102 and the two optical axes 112) at a known point. It will be appreciated that a reference plane can be made perpendicular to the optical axis 102 of the projection lens 32 at the point of intersection. This reference plane is behind the corneal surface.

Tyndall images of the illuminated points 36 in the object plane of the projector 108 are then produced at locations, in X and Y terms, that are a direct function of the sagittal depth of the cornea at each of the several image points so illuminated. The displacement of any given image point from the locus of intersection with the reference plane 2 is, in turn, directly related to the sagittal depth at that particular image point. The pair of images is viewed by the paired television cameras 3,4 to define simultaneously, in X and Y terms, the location of the points so illuminated.

Clearly, the surface geometry can be produced by a single camera 4 since all of the geometric data are available for such a definition. However, the present invention makes use of dual, stereo image pairs to increase the accuracy of measurement by (1) comparison of the simply derived X, Y, Z data from each image as well as (2) direct stereoptic reconstruction of the surface. This multiple reconstruction system provides an accuracy check as well as a means for eliminating spurious reflections from the corneal surface by objects or lights which might be present in the images.

The images from the paired cameras are converted into digital form by a sampling system commonly called a frame grabber. The stored digital images are compared in the associated computer, first by sequential subtraction to extract the target data from the background clutter and then left to right geometric comparisons are made to determine the location in three space of the reflecting surface.

In an alternative embodiment, the television cameras 4 are so structured as to provide a digital representation of the video information as opposed to the common analog data output. The digital data take the form of byte wide serial transfer of brightness information.

As described above, a small numerical aperture for the projection lens 32 assures adequate depth of focus so that diffuse reflections of the imaged points are sharply defined over the depth of the anterior chamber and corneal thickness. To compensate for the small lens area, the illumination source 31 must be quite bright. In turn, the energy at the cornea from the light source 31 must not produce any measurable heating of the eye tissues. This task is accomplished by using an arc discharge type gas filled lamp having a flash duration that is short but bright. The pattern illumination is rendered in high contrast while the average power is kept quite low to achieve the desired goals. The lamp flash is controlled in time synchronism with the television camera vertical interval by the computer type controller of the system. At intervals, preferably about one second, the tube (lamp) 31 is flashed and the image of the diffuse reflection of the projected spots is captured by an analog to digital conversion of the paired television images. In an alternative construction, the lamp may take the form of a solid state light emitting device.

The general room illumination, reflections from nearby objects, and the like present a cluttered image that contains much extraneous information. To remove this clutter from the calculations, the present invention provides a spectral and temporal selection system that enables a reduction in the complexity of computation required for deriving the spatial data that represents the corneal surface shape.

The first method for reduction of this extraneous information is the limitation of the spectral content of the light from the target by insertion of suitable optical band pass filtration m the illumination path and similar filters in the television camera lens systems 10. The inherent sensitivity of silicon-based integrated circuit image sensors is the basis for the selection of the near infra-red (IR) for the filters. With the use of the IR filters, the room ambient illumination is attenuated by a large amount while the target reflections are not.

The second method of reducing noise employed in the present invention involves synchronizing the time sequencing of the target illumination with the television camera timing. In this method described above, an image is received, digitized, and stored with the target illumination turned off. A second pair of images is subsequently acquired in similar manner with the target illumination provided. The first pair of images is numerically subtracted from the second pair so that any portions of the images that are substantial identical cancel, while the target image that exists only in the second exposures remains intact. The identification of the image points to be used for surface shape determination is then made by a simple numerical thresholding technique that removes the residual, noise induced, pictorial data that is not related to the desired target reflections from the paired viewing angles.

In the first method, which is directed to spectral selection, suitable IR optical bandpass filters are selected. The charge coupled device is inherently sensitive to near infra-red with a peak sensitivity at or near 750 nanometers. Optical filters with a low wave pass including this wavelength over the light source 31 and camera lenses 10 provide the removal of the background signal so that the data processing of the pictorial data is greatly simplified. The subject would not be aware of the measurements since the infra-red light is not visible to the human eye. By pre-processing the video data stream in this fashion, the paired camera video streams can easily be processed at a rate adequate for almost real time data display without excessive cost per system.

In the second method described above for reducing noise employed in the present invention, the illumination of the target is alternately turned on and off in sequential image times. It follows that if two identical pictures were to be subtracted from each other, then the resultant image would be nil. In this case, however, there is a difference between the two images because of the action of the sequential illumination. This subtraction technique provides a less cluttered image from which the corneal shape can be derived by simpler computation, which is, therefore, faster and cheaper.

As described above, conventional television cameras 3,4 are mounted on a conventional pedestal unit with associated head rest for providing paired images of the reflection of the illuminated targets points 36 from the cornea. Sub-miniature television cameras 3,4 with adequate sensitivity and resolution are obtained quite cheaply and installed with suitable lenses 10 to provide coincident images from two known angles relative to the optical axis 102 of the matrix projector 108. The paired cameras 3,4 generate the electronic images of the reflection to be analyzed.

The angles are established by the distance between the camera lens axes 112 and the projector optical axis 102. These factors are known, and so the angular position of the camera focal plane and lens optical axis 102 are established in manufacture. (As will be obvious to one skilled in the art, the angles can be made adjustable if interchangeable lenses are to be employed).

In the apparatus of the present invention, the location of the principal points of the projector 108 and camera lenses 10 are accurately known by construction and test. Also, as described above, the optical axis (centerline 102) of the projector 108, and the optical axes 112 of the cameras 3,4 converge in a single point in three space, The axial distance and angle from the image points is then defined in the same manner as is disclosed in my previous patent, U.S. Pat. No. 5,512,965.

For each data point recovered from the first camera 4 coupled with the corresponding point from the second camera, calculations are made of the location on the corneal surface in three space coordinates. All corresponding reflections in each image pair are examined in a similar fashion. In this manner, the triangulation calculations establish a matrix of known surface points in three dimensions. A complete, or substantially complete, surface shape definition is constructed from the calculated location for many surface reflection points.

Figure 4:
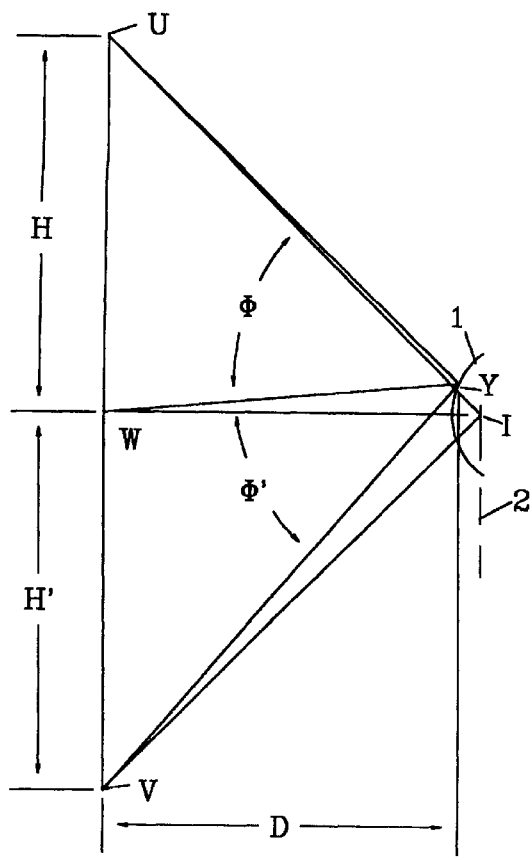
FIG. 4 is a schematic illustration depicting the optical geometry employed in the present invention.

Referring now to FIG. 4, which illustrates the geometry related to the triangulation method employed in the present invention. FIG. 4 shows the eye 1 and a point Y which corresponds to an image point formed on the eye. The front principal points of the paired camera lenses 10 are located at points U and V with their respective optical axes 112 defined by lines UI and VI. Where the point, I lies in a plane of reference 2 perpendicular to the projection axis 102. Similarly, the line WI corresponds to the optical axis 102 of the projector 108. The distance to the corneal surface of the eye 1 is roughly established by the operator who positions the instrument 100 to focus on or slightly behind the corneal surface. The front principal point of the projector lens 32 is located at a point W with the distances H and H' established by construction of the system As shown in FIG. 4, the two reference triangles, WIU and WIV, are coplanar. However, a discrete point 36 projected onto the cornea may lie in some plane above or below the plane defined by the two reference triangles.

The corneal surface is then defined by three effectively independent sets of calculations. The measuring rays from any given reflection are defined by triangles UYW and VYW. For any single projector image point Y on the cornea, angles Φ (UYW) and Φ (VYW) can be established. Solution of the axial distance from Y to the system baseline UWV is by conventional trigonometry. Each triangle yields a solution for the distance with the composite solution producing a considerable accuracy enhancement over a single triangle solution of the prior art. The illustration of FIG. 4 is representative of the optical system geometry which will be understood to comprise a volume of space containing the entire cornea of the eye being examined.

The present invention offers numerous advantages over the prior art, in particular, the technique described by Hjalmar Gullstrand in the last century. The most significant problem with the Gullstrand technique is that the central point is not measured; rather, the central point from which the surface must be defined is calculated from tangent slopes. The underlying assumption is that the central portion of the cornea is spherical and symmetrical In fact, the central portion of the cornea is neither spherical nor symmetrical. In the present invention, two surface constructions are made by triangulation, and these are combined by a second triangulation for removing the inherent errors of the prior art systems. The trigonometric derivation from the stereo pair data base is of better overall quality than the tangent slope derived models of the prior art measurement.

To fully understand this invention, some knowledge of television signals is required. A television image that seems to the viewer to be a single stable image is, in fact, a blank screen most of the time. By making use of the persistence of vision and other psycho-physiological phenomena, the human visual system is tricked into perceiving a whole picture.

The picture is drawn by a beam of electrons that strike a phosphor coating inside the faceplate or viewing surface of the cathode ray tube where the image is formed. The phosphor emits visible light in direct proportion to the number of electrons per unit time that like it and the energy of the particles in the beam. The beam is formed by thermal emission and electrostatic acceleration in an "electron gun" within the neck of the tube that is behind the viewing surface and, thus, out of view. The beam is focused by an electrostatic lens within the gun assembly so that the screen phosphor area that is bombarded at any instant is quite small compared to the entire screen. The illuminated spot is on the order of a few thousandths of an inch in diameter. This area is the only area on the entire screen that emits light to any significant extent at any given instant.

As illustrated in FIGS. 5 and 5a, which depict a television raster, the beam is swept over the surface of the faceplate in a regular pattern called a raster 30. Where the beam is incident on a particular area 28, that area is illuminated. In contrast, the areas 29 where the beam is not incident remain dark. This pattern was selected to permit a complete image to be formed without objectionable flicker and to limit the amount of radio spectrum required to transmit the information to the home.

The raster 30 is generated by deflecting the beam of electrons by an electromagnet assembly called a yoke. The beam is driven to the upper left corner (as viewed) at the start of each picture interval. The beam then sweeps across the faceplate from left to right to the other edge of the screen. At that time, the beam is turned off or "blanked" for a short time while the yoke signal is changed to start a new line at the left edge of the screen slightly below the first line. After this retrace interval, the beam is unblanked and the process is repeated. The actual image or frame is made in two interdigitated fields, each of which is, in theory, made up of 262.5 such lines (some of these lines do not result in any image formation but are outside the viewing area).

As the raster 30 is drawn, the intensity of the beam is modulated by the incoming signal so that the intensity of the light produced per unit area is a faithful reproduction of the transmitted scene. The image can be thought of as many discrete areas or picture elements (pixels) which are painted on the screen in time sequence. The area of a pixel, the smallest discrete pictorial element, is limited by the information transfer rate available. This rate was set for commercial broadcasting to fit in the amount of radio spectrum available. The NTSC (domestic broadcast standard) limits the rate of information to 4,500,000 elements per second.

The transmitted signal also contains synchronizing information required to keep the locus of the beam in step with the source at any time to insure undistorted restructuring of the sequential data into a picture. In particular, sync signals are included in the transmitted signals. The sync signals are included in the transmission as a part of the horizontal and vertical blanking intervals.

FIG. 6 shows the voltage waveform of a single raster line of video information. In particular, FIG. 6 illustrates the voltage amplitude or brightness versus time relationships. One horizontal line electrical signal is illustrated showing the timing and amplitude relationships of the signal. The electrical waveform illustrates a single line of the raster with alternating black and white areas. The horizontal sync pulse 22 is superimposed on a blanking signal 23 of such amplitude as to insure that the beam in the display is fully off during the retrace interval. Each successive raster line starts at the left edge, as viewed. The video signal, in this case at black level 24, is followed by four white areas 25. The definition of black and white are in terms of relative voltage magnitude above the "porch" or blanking level. There are two amplitudes that are predefined limits for the negative (black) and positive (white) voltages. The more positive clamp level is called the white clip level 26 and the video signal voltage is limited to this level when over bright objects or areas are photographed. The black clamp level 27 is adjustable based upon a sample of the image at a selected reference point This is called keyed clamping.

The time between the horizontal sync signals in the NTSC standard is $\frac{1}{15750}$ second or 63.4 microseconds. The horizontal rate is 15,750 lines per second and the field and frame rates are 60 and 30 per second, respectively. From this, it follows that the pixel size can be defined in either size or time domain.

In conventional broadcast television the signal is limited to 4.5 Megahertz that yields a pixel rate of only 236 for the active or visible line of some 52.4 microseconds. The overscan of the display means that even fewer pixels make up the actual image viewed by the user. Even fewer elements are available for display in common cassette recording devices. These facts limit the inherent resolution of a television picture to a level much less than even a poor photograph, but the apparent motion and several other factors cause the perceived image to be acceptable when used as an entertainment medium.

For image analysis to perform the photogrammetric functions of keratometry, a higher resolution camera system is desirable. However, a high resolution can impose the problem of requiring more data to be analyzed to produce the corneal map.

As described above, the television cameras 4 may include charge coupled devices. A common, so-called charge coupled device solid-state camera uses an integrated circuit array of photoelectric cells arranged in rows and columns. A typical solid-state camera might have 525 or more elements (i.e., photo-diodes) in each line. The number of pixels per line will establish the pixel pitch or inherent resolution limit of a video camera which uses such a device in lieu of the more common vidicon or similar vacuum tube pickup element. It will be appreciated that the technique of the invention reduces the number of pixels required for analysis by employing a novel time sequence comparison method to permit the computer solution to be derived faster and with fewer steps and pixels.

Figure 7:
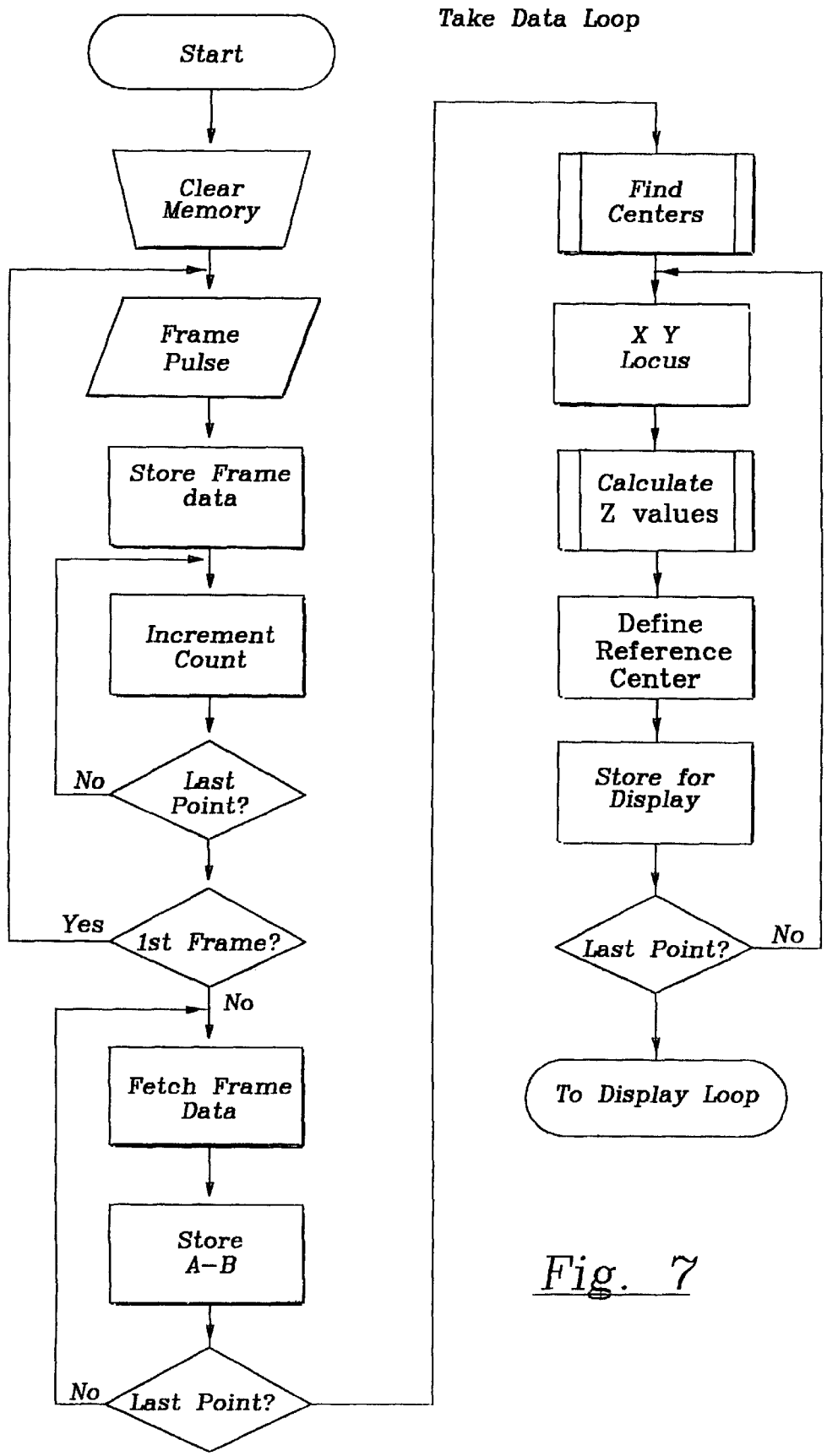
FIG. 7 is a program flowchart depicting a portion of the logical operation of the present invention.

Referring now to FIG. 7, which shows a sequence of operations employed in the present invention that is controlled by the associated computer. A portion of the program sequence is illustrated for explanation of a representative embodiment of the present invention.

The start of data acquisition is controllable by operation of a switch, 17 button or other control after alignment and focussing by conventional technique.

For a single data acquisition sequence, two successive video image pairs are captured. The target matrix 34 illuminated for the second image time in the sequence. At the time when a vertical blanking pulse is accompanied by a first field identification pulse, the sequence is begun. The digital data sequence from the television cameras 3,4 and the frame grabber 14 represents the brightness of each of the sequential pixels that comprise the pictorial information. These data points are placed in sequential loci in the associated memory computer system that serves to define the storage location of each element received. The process continues until the last pixel of the current picture pair is captured. Then the target matrix illumination is turned on and the sequence is repeated thereby storing the second picture pair in additional memory locations.

After both sequential image pairs have been captured and stored in this manner, the content of the areas of memory that contain the first and second picture from each camera 3,4 are compared by subtraction on a pixel by pixel basis. In the event that no image of the reflection of a target matrix point 36 is encountered at the instant location, the numerical result of the subtraction will approximate zero. The value may not be exactly zero because each picture contains some degree of noise; however, the magnitude of the number so derived will be small compared to the alternative condition in which a target matrix reflection is encountered in the second exposure data from either camera 3 or 4. The data points with non-zero values, so defined, represent the reflected image of the target matrix 3 from the different camera angles. These points are stored in another portion of the memory for further processing and ultimately for display.

In an alternative embodiment, only the pair of images containing the illuminated matrix image are defined for storage and analysis. In this configuration described above, the target matrix 34 is provided with an infra-red pass filter as are the camera lenses 10. In this embodiment, only the images of the matrix points 36 are imaged so the subtraction process is not required. The calculations are more complex, but the time required for image capture is reduced by one half. Both systems may be contained m a single instrument with the user selecting the operational mode by a suitable switch or other command input.

The stored data pairs are then treated in conventional software programs to extract the X, Y location of all image points. The most common of these programs uses a matrix technique for examining a group of adjacent loci to determine the exact center of each image point on a point-by-point basis. After the image points are so identified, the known size of the image (based on data from a calibration table data) is compared with the apparent location from the video data. Simple trigonometric calculations provide the spatial data from the raw X, Y data pairs. Comparison between the sequential calculation from the paired images provides a means for rejection of erroneous points caused by system or image noise. This sequence continues until all data points for each of the two camera sources 3,4 has been calculated. The surface shape, as defined from two known angles, are then combined to provide a smooth surface curvature map for display by conventional techniques.

The present invention advantageously employs two cameras 3,4 in determining the surface curvature map. A single camera surface measurement has limited ability in determining the location of the center or centroid of points formed on a side of the cornea which is furthest from the camera 3 or 4 and slopes away from the camera Angles corresponding to rays that come close to being tangent with the surface of the eye 1 and that slope away from the camera 3 or 4 and the projector 108 pose a problem. In contrast, the dual camera system of the present invention, which provides two cameras 3,4 that are directed at different portions of the eye 1, provides broader coverage over the eye. The coverage of each camera 3 or 4 also advantageously overlaps each other at the central zone of the cornea, thus, providing additional coverage for the most important region of the eye 1.

As described above, the images from the paired cameras are converted into digital form by a sampling system commonly called a frame grabber. The stored digital images are compared in the associated computer.

In an alternative embodiment, the television cameras 3,4 are so structured as to provide a digital representation of the video information as opposed to the common analog data output. The digital data take the form of byte wide serial transfer of brightness information.

This data storage format simplifies the data processing steps in which the subtraction process compares numerical brightness values. The upper and lower byte at each location defines the video data from the pair of cameras 3,4 while the sequential data location for storage of the second pair of pictures differs from the first pair by the state of a single, high order, address bit. The computer program is simplified by this addressing method because the paired data for the sequential frames are at identical loci except for a flag bit that is used as the most significant address bit. The initial subtraction step for removing the background information is made by setting the fag bit and reading the data as the addend, and then resetting the flag bit and reading the data as the augend with the sign bit inverted. The resultant is then stored in memory as the difference between the time sequenced picture pairs. The data, thus stored, is then compared on a bit-by-bit basis against a numerical threshold amplitude value. The logical result is stored in a matrix that represents the X Y coordinates of the reflection of the target matrix for trigonometric evaluation of surface shape.

Prior to processing the video information, the instantaneous amplitude of the signal is converted into digital amplitude information by conventional "flash" A/D conversion and the data stored in a conventional random access memory. In conjunction with this data retrieval and conversion system, and in time synchronism with it, is a lamp control circuit which causes the projector lamp 31 (which may be of the gas discharge type) to be turned on for alternate non-interlaced fields of the video.

Since the target 34 is illuminated for one field and extinguished for the second, there is a difference between the two sequential video frames in that only one includes the pattern generated by the reflection from the corneal stroma of the target matrix 34. The second frame data, obtained while the lamp 31 is off, is digitized as was the first frame. At the same time, the memory contents that define the numerical representation of locus brightness from the first frame are extracted and numerically compared to the current value. A comparison between the first frame and the second frame is possible because the eye 1 is stationary and the time domain is controlled by a synchronizing signal source of high stability. It follows that the numerical difference between the two sequential points that describe the same spatial point will be very low in the areas of no target image and high in the areas of the image.

This subtraction will provide a new set of data points in numeric form for analysis that may be subjected to the edge detection means previously described to reduce the number of points to be analyzed. In practice, the two defined image points (less background clutter) from the cameras 3,4 may be averaged and compared with a preset value to determine which points are valid, and therefore, should be saved. It should be noted that the storage must involve both the magnitude and the screen locusin order for the computer analysis to define the shape of the reflections. If there is not good agreement of the X, Y, Z locus between the two camera definitions of a point's location, the point would be discarded. This electrical analog of the image from the corneal stroma forms the basis for the contour measurements to be performed.

As describe above, projector system 108 forms an image of the target matrix 34 on the eye 1. The target matrix 34 comprises a pattern of transparent points 36. The pattern of transparent points 36 that is to be obtained is determined by (1) the desired areas to be defined, (2) the resolution to be obtained in the spatial definition, and (3) the computer program size and speed available. The central zone, which is about 3 millimeters in diameter, contains the primary image forming section of the corneal "lens." This central zone is the most important area to vision. Consequently, the measuring points 36 are closer together in this area. When the points are situated closer together, more calculations must be completed to define the centroids. Likewise, more computation is required to arrive at a smooth surface for display. However, the clinician desires systems that provide data quickly and within a reasonable error range. Unfortunately, solving more calculations in a fixed time frame requires a system that is more powerful and, hence, more expensive.

The depth of focus of the projection system 108 for providing the matrix of points to be used for keratometric determination should be as high as possible to reduce defocusing with variation of lens 31 to eye 1 distance. An acceptable blur spot is related to the pixel pitch of the camera system 4. This spot size must be small enough that it will have no adverse effect on the image to be digitized.

The convergence angle of the beam is related to the focal distance to the object plane and the focal ratio of the lens 31. The aperture sine must remain small for the depth of focus to be adequate for the depth of the anterior chamber plus some extra amount to compensate for mis-positioning of the keratometric apparatus of the present invention. The actual calculations for these definitions are well known in the art and are not detailed here.

The use of simple lens projection coupled with the required small aperture causes illumination of the charge coupled device in the cameras 4. To substitute for a variation of video gain required for linearization of video response, a novel system is employed. The essentially parabolic loss curve from center is characterized and a zone type neutral density filter 35 with inverse transmission is interposed in the illumination path of the projector 108.

With the apparatus of the present invention, capture of the paired images is preferably by paired analog to digital converters but in an alternative construction, the data streams are time division multiplexed to a single analog to digital converter. The advantage lies in the common amplifier and reference which reduces errors, but the single converter system requires much faster memory and amplifier components which increases production costs.

As described above, the cameras 3,4 may comprise charge coupled devices. However, other suitable detectors 3,4 may also be employed in the practice of the invention Examples of other detectors 3,4 suitably employed in the apparatus and method of the present invention include vidicons and similar vacuum tube pickups.

The most common integrated circuit charge coupled device camera photosensitive matrix is about one-third inch (approximately 9 millimeters) in diagonal measure. The topical limbus of the normal human eye is on the order of about 12 millimeters in diameter. The camera must provide an image of this entire area for analysis. The desired image is on the order of about four millimeters in diameter (or somewhat less) to allow all of cornea to the limbus, with the target matrix reflection to be seen in all cases. The size of this image is chosen to meet the previous limitation so that the outer reflection will be visible in the television picture with a minimum of extra coverage. The vertical size of the picture is less than the horizontal by a ratio of 3:4 (FIG. 5). The desired image must fill ¾ of the charge coupled device faceplate, or somewhat more, allowing for the normal overscan and the fact that the image must fit within the picture area irrespective of the limbal diameter. Consequently, the image of the target reflection will be on the order of about four millimeters in diameter.

The image of the 12 millimeter limbus will be close to the frame height of ~four millimeters so a magnification ratio of 1:3 is chosen. The conjugate ratio is numerically equal to the magnification ratio which establishes the length of the optical paths 102 and 112 for any given focal length of lenses employed.

FIG. 8 shows an arrangement between the photo-sensitive area of the detector 37, of the camera 3 or 4, the camera lens 10, and the eye 1 being examined as employed in the present invention. As shown in FIG.8, the image and object planes are not parallel to the optical axis 112 of lens 10.

Optical image degradation occurs when the image and object planes are not both parallel and perpendicular to the optical axis 102 of the projection lens 32. In ophthalmic photography, and for keratometry in particular, the object plane is inclined to the optical axis and the conjugate ratio is on the order of 1:3. Accordingly, the lens and focal planes must be rotated to provide best overall image sharpness. The Scheimpflug principle is used to accomplish this task. Specifically, the Scheimpflug principle is employed for depth of field improvement. The reduction of geometric distortion in photographs by the Scheimpflug rule or law is well known to commercial photographers, and the application of this principle in keratometry is contained in my previous patent, U.S. Pat. No. 5,512,966. When an object at a near point is not parallel to the focal plane of the camera, a photograph will demonstrate the distortion where parallel planes of the object seem to converge in the photograph. In addition, the depth of focus is often inadequate to render sharply all portions of the object to be photographed.

The small subject distance involved in ophthalmic photography by a conventional slit lamp camera exaggerates this pictorial distortion. The angle of the optical axis of the microscope to the optical axis of the camera places the image in a plane which is not perpendicular to the optical axis of the camera. In addition, the design of the camera system which uses the bio-microscope for image sourcing imposes a severe limit on the faceplate illumination of the camera. At common magnifications, the system if on the order of f16, requires that large flash energy levels be employed for adequate exposure with high resolution color film.

In the present invention, orientation of the cameras 3,4 and lenses 10 are adjusted to improve the depth of field.

The distortion introduced into the photographic image is related directly to the angular relationship employed. To compensate for the stretching of the image, the individual television raster line is compensated by application of simple geometry. The photographic image, as projected in a Scheimpflug rule focus compensated system, is in a plane that is at a defined angle to the optical axis 112 of the lens 10. FIG. 8 depicts this Scheimpflug rule focus compensated system.

The process used to compensate for the stretching of the image requires that the image be compressed in the horizontal axis, which effectively increases the number of pixels per linear segment. Calculation of the X, Y loci before the compression to remove the Scheimpflug induced distortion provides the greatest accuracy in the shape determination because the number of pixels for a given surface area is increased over the undistorted values after compensation.

This process is preformed in instrument calibration by careful analysis of the images on flat planes at several known distances from the projector lens. A matrix or mathematical correction system constructed from these data serves to provide the geometrical correction for the construction of an accurate topographical map representation of the corneal surface area to be measured. The recalculation of the image to remove the distortion requires that this interpolation be performed to provide a smooth display of the surface geometry profile.

To further minimize the optical image degradation that occurs when the image and object planes are not both parallel and perpendicular to the optical axis 102 of the projection lens 32, the lens aperture must be at or near minimum for best depth of focus; this solution requires high light levels, which could cause retinal heating. To provide the required light without high average energy levels at the cornea, a short high intensity flash illumination source is employed (as described above) to reduce the energy entering the eye for safety reasons.

With regard to resolution, it will be appreciated that the resolution figures quoted by the builders of television cameras are not a true indication of the resolution obtainable with the present invention because these resolution figures are derived from modulation transfer functions that contain limitations imposed by the expected use. In the application of the present invention, the spatial frequency of the target matrix 34 is predictable and the effective system resolution can be made higher than the limit predicted by the manufacturer's specification sheets.

Additionally, the resolution of the data stored in the present invention is not a function of the memory size of the host system and, thus, permits the definition of the image to a much higher resolution limit than would be possible with direct digitization of the image and conventional image analysis algorithms as are used in the prior art.

The technique employed by the present invention results in a substantial reduction of the number of data points that must be treated in the computer while retaining a degree of data redundancy that permits the system to reject noise contaminated data points by conventional signal averaging. This processing substitutes for the conventional software system and, the computations are simple and quick. Based upon this redundancy in the data to assure the accuracy of the measurement, there is no requirement for a large and complex computer and program system to derive the desired curvature values and the simple calculations are quickly performed.

Each target reflection produces one data point at each reflection point that is identified on the anterior corneal surface and, therefore, corneal surface shape. Further, the numerical scatter of the data points is a function of the focus and overall image quality. Accordingly, each measurement can be evaluated for minimum acceptable quality. A decision can then be made whether to reject any measurement that does not fulfill the quality standard set into the software.

When an image set has been stored by the previously detailed technique and the requisite computations performed in the computer, the digital information for defining the corneal shape can be presented for use in any of several formats that are well known in the art.

Several computer generated data display formats are made available. These range from a numerical axis and magnitude in the eyepiece to computer CRT monitor displays such as a vector map with a line showing both axis and magnitude. The display may be with or without a series of concentric circles representing cylinder magnitude to give rapid assessment of astigmatism and to permit the surgeon to select a value that will result in the least residual astigmatism after healing is complete.

The user is most often interested in data presentation in terms of diopters variation from true symmetry of the cornea, and the conversion of the topographic data into dioptric form is trivial. Display of the derived data may be in graph form for ease of assimilation and application by the user. This is by means of conventional display algorithms and techniques that are machine dependent and will not be discussed in detail.

In an alternative embodiment, not illustrated, instead of the view of the eye through the microscope eyepiece 9, a third television camera is employed for visual alignment and focus via the conventional computer display monitor mounted within the view of the user. The remote monitor system is less expensive but not as easily operated.

Thus, it can be seen that this system substitutes novel means and method for the conventional image analysis technique to permit the construction of a very inexpensive system that can be used to produce clinically useful data. In particular, the present invention uses a unique system of video image analysis to provide to the user full topographical mapping of the cornea Almost it display of the corneal radius at enough points to permit accurate assessment of the surface shape is provided. The use of a dual imaging system for providing accurate stereopsis and consequent surface mapping in the present invention is a significant improvement over the presently available techniques. The surgical keratometer system of the present invention is designed to eliminate most of the instrument related problems and to address the operational limitations in such a way as to provide the greatest safety and accuracy possible.

Prior art systems such as that described in U.S. Pat. No. 3,797,921 and others provide only a tangent slope calculation that can be in error due to (1) improper focal distance without the user being aware of the error and (2) the invalid assumption of an axial radius of curvature such as would be produced by spherical surfaces. In contrast, the present invention provides a system of cross checking to ensure the accuracy of the corneal shape data. The system of the present invention also reduces the effect of lens to object distance that might result from inaccurate focusing by the operator; see above-mentioned U.S. Pat. No. 5,512,965.

The surgical keratometer of the present invention makes use of a microcomputer to provide fast and accurate measurements without the limitations of the other available systems. With careful use, the system will consistently provide information to the clinician to quantify the surface shape as the therapeutic procedure is being conducted so that the surgeon may better judge the results.

Thus, there has been disclosed a method and apparatus for measuring surface topography and local thickness of a cornea The method and apparatus of the invention for measuring the topography of a cornea can be applied to clinical procedures and, in particular, to corneal scar and ulcer measurement and contact lens fit. The foregoing descriptions of one embodiment of the present invention is representative of the techniques employed and these descriptions are not intended as a limit on the scope of the invention. It will be readily apparent to those skilled in this art that various changes and modifications of an obvious nature nay be made, and all such changes and modifications are considered to fall within the scope of the invention, as defined by the appended claims.

What is claimed is:

1. An instrument for measuring surface topography of a cornea for clinical diagnostic purposes without introduction into the eye of any fluorescing substance, said instrument comprising:
   a) an optical projector that projects a pattern onto said cornea, said pattern comprising a plurality of isolated points;
   b) a first camera and a second camera with each comprising a camera lens and a detector array, said first camera, said second camera, and said projector directed toward a single point on the cornea constituting a main point, said first camera and second camera producing an image pattern of said plurality of isolated points including the main point projected on said cornea the with diffuse reflection in the bulk of the cornea, location of each of said isolated points on said cornea being a function of and dependent upon the surface topography of the cornea;
   c) a computer receiving digital data representing said isolated points on the cornea and using triangulation evaluations to determine said surface topography of the cornea from said location of said isolated points and utilizing said main point on said cornea; and
   d) a display for displaying said surface topography.

2. The instrument of claim 1 wherein said first camera and said second camera image said cornea for a first time interval during a portion of the time when said pattern is projected on said cornea and for a second time interval during a portion of the time when said pattern is not projected on said cornea, and wherein signals representing said image pattern obtained during said second time interval are subtracted from signals representing said image pattern obtained during said first time interval, thereby removing undesirable background information.

3. The instrument of claim 1 wherein a filter having a transmission pattern to compensate for image brightness variation is placed between said cornea and a light source therefor.

4. The instrument of claim 1 wherein said projector comprises a light source, a projection lens, and a target therebetween, said target being located to enable said plurality of isolated points to be formed thereon, said light source illuminating said target and said projection lens.

5. The instrument of claim 1 wherein said optical projector further comprises an alignment microscope having at least one eyepiece and said first camera and said second camera are attached to said alignment microscope.

6. The instrument of claim 5 wherein said projected image pattern is visible through said eyepiece.

7. The instrument of claim 1 wherein said surface topography is determined during clinical diagnostic testing.

8. The instrument of claim 1 wherein said image pattern of isolated points projected on said cornea is obtained simultaneously from said first camera and said second camera.

9. The instrument of claim 1 wherein said display of said surface topography generates a contour map of the surface of said cornea.

10. An instrument for measuring the surface topography of a cornea, said instrument comprising:
   a) an optical projector that projects a pattern onto said cornea, said optical projector having an optical axis, said pattern comprising a plurality of isolated points;
   b) a first camera and a second camera each operating in temporal synchronism with one another and each comprising a camera lens and a detector array, each said camera having an optical axis, said optical axis of each of said first camera, said second camera, and said projector intersecting at a single point, said first camera and second camera producing an image pattern of said plurality of isolated points which are projected on said cornea, each of said cameras producing an image with the projection of a pattern to provide a first image pair, and producing an image without projection of the pattern to produce a second image pair, the location of each of said isolated points on said cornea being a function of and dependent upon said surface topography of the cornea;

c) means associated with said cameras receiving signals representative of each of said image pairs to subtract one image of each of said pairs from the other image of each of said pairs;

d) a computer processor receiving digital data representing said isolated points on the cornea and using triangulation evaluations to determine the surface topography of the cornea from said location of said isolated points on said cornea; and e) a display for displaying said surface topography.

11. The instrument of claim 10 wherein said projector comprises a light source, a projection lens, and a target therebetween, said target comprising said pattern of isolated points formed therein, said light source illuminating said target and said projection lens, said optical axis of said projector corresponding to said optical axis of said projection lens.

12. A method of measuring surface topography on a cornea during clinical diagnostic procedures, said method comprising the steps of:

a) projecting a pattern onto said cornea using a projector, said pattern comprising a plurality of discrete points, said location of each of said discrete points in said pattern on said cornea being a function of and dependent upon the surface topography of the cornea;

b) directing a first camera and a second camera operating in temporal synchronism with one another, and said projector toward a single point in space, each of said cameras comprising a camera lens and a detector array;

c) placing said cornea at a position between said single point in space and said first camera, said second camera, and said projector;

d) obtaining the image pattern of said discrete points projected on said cornea with said first camera and said second camera;

e) also producing an image of the cornea with each said first and second camera without projecting the pattern onto the cornea;

f) subtracting signals representative of the image with the pattern from each camera from signals representative of the image from each camera without the projected pattern;

g) a employing triangulation evaluations to determine said surface topography of said cornea from the location of said discrete points in said pattern on said cornea; and h) displaying said surface topography.

13. The method of claim 12 wherein said first camera and said second camera image said cornea for a first time interval during a portion of the time when said pattern is projected on said cornea and for a second time interval during a portion of the time when said pattern is not projected on said cornea, and wherein signals representing said image pattern obtaining during said second time interval are subtracted from signals representing said image pattern obtained during the first time interval, thereby removing undesirable background information.

14. The method of claim 12 wherein a first filter having a first transmission band in the infrared region is placed between said cornea and a light source used with said projector, and a second filter having a second transmission band in the infrared region is placed between said cornea and each said detector array in each said camera, said first and second transmission bands overlapping.

15. The method of claim 12 wherein said projector comprises a light source, a projection lens, and a target therebetween, said target being located to have said plurality of discrete points to be formed thereon, said light source illuminating said target and said projection lens.

16. The method of claim 12 wherein said optical projector, said first camera, and said second camera, are attached to a microscope means, said microscope means being arranged to provided alignment control for said projector and the said cornea.

17. The method of claim 16 wherein said microscope includes at least one eyepiece, said eyepiece being arranged so that said cornea is visible through said eyepiece.

18. The method of claim 12 wherein said topography is determined during clinical diagnostic procedures.

19. The method of claim 12 wherein said image pattern of discrete points projected on said cornea is obtained simultaneously from said first camera and said second camera.

20. An instrument for measuring the surface topography of a corena without introduction into the eye of any fluorescing substance, said instrument comprising:

a) an optical projector that projects a pattern onto said cornea, said optical projector having an optical axis, said pattern comprising a plurality of isolated points;

b) a first camera and a second camera, each operating in temporal synchronism with one another and each comprising a camera lens and a detector array, each said camera having an optical axis, said optical axis of each of said first camera, said second camera, and said projector intersecting at a single point, said first camera and second camera producing an image pattern of said plurality of isolated points which are projected on said cornea, with diffuse reflection in the bulk of the cornea, the location of each of said isolated points on said cornea being a function of and dependent upon said surface topography of the cornea with diffuse reflection in the bulk of the cornea;

c) a computer processor receiving digital data representing said isolated points on the cornea and using triangulation evaluations to determine the surface topography of the cornea from said location of said isolated points on said cornea; and d) a display for displaying said surface topography.

21. A method of measuring surface topography on a cornea during clinical diagnostic procedures without introduction into the eye of any fluorescing substance, said method comprising the steps of:

a) projecting a pattern onto said cornea using a projector, said pattern comprising a plurality of discrete points, said location of each of said discrete points in said pattern on said cornea being a function of and dependent upon the surface topography of the cornea;

b) directing a first camera and a second camera operating in temporal synchronism with one another, and said projector toward a single point in space, each of said cameras comprising a camera lens and a detector array;

c) placing said cornea at a position between said single poiknt in space and said first camera, said second camera, and said projector;

d) obtaining the image pattern of said discrete points projected on said cornea with said first camera and said second camera with diffuse reflection in the bulk of the cornea;

e) employing triangulation evaluations to determine said surface topography of said cornea from the location of said discrete points in said pattern on said cornea; and f) displaying said surface topography.

22. The method of claim 21 wherein said first camera and said second camera image said cornea for a first time interval during a portion of the time when said pattern is projected on said cornea and for a second time interval during a portion of the time when said pattern is not projected on said cornea, and wherein signals representing said image pattern obtaining during said second time interval are substracted from signals representing said image pattern obtained during the first time interval, thereby removing undesirable background information.

* * * * *